United States Patent
Kitaevich et al.

(10) Patent No.: US 6,471,872 B2
(45) Date of Patent: *Oct. 29, 2002

(54) HEMOFILTRATION SYSTEM AND METHOD BASED ON MONITORED PATIENT PARAMETERS

(75) Inventors: Yuli Kitaevich, Loveland, OH (US); Nat Hemasilpin, Fairfield, OH (US); J. Gabriel Marchevsky, Cincinnati, OH (US); John J. Bissler, Cincinnati, OH (US); George Benzing, III, Cincinnati, OH (US); Paul T. McEnery, Cincinnati, OH (US)

(73) Assignee: Children's Hospital Medical Center, Cincinnati, OH (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/814,160

(22) Filed: Mar. 10, 1997

(65) Prior Publication Data

US 2001/0045395 A1 Nov. 29, 2001

Related U.S. Application Data

(63) Continuation of application No. 08/478,942, filed on Jun. 7, 1995, now abandoned, which is a continuation-in-part of application No. 08/299,899, filed on Sep. 1, 1994, now abandoned, which is a continuation of application No. 08/062,928, filed on May 17, 1993, now Pat. No. 5,344,568, which is a continuation of application No. 07/775,183, filed on Oct. 11, 1991, now Pat. No. 5,211,849.

(51) Int. Cl.[7] .......................... A61M 1/34; B01D 61/00; B01D 61/18; B01D 61/22

(52) U.S. Cl. .......................... 210/739; 210/85; 210/90; 210/96.1; 210/97; 210/134; 210/138; 210/143; 210/195.2; 210/257.1; 210/258; 210/321.71; 210/416.1; 210/433.1; 210/645; 210/646; 210/650; 210/805; 210/929; 604/4.01; 604/5.01; 604/65; 604/66; 604/67

(58) Field of Search .......................... 210/85, 90, 96.1, 210/97, 101, 134, 138, 143, 195.2, 257.1, 257.2, 258, 259, 321.71, 416.1, 433.1, 645, 646, 649, 739, 805, 929, 650; 604/4, 5, 6, 66, 4.01, 65, 67, 5.01; 422/48; 177/45, 50

(56) References Cited

U.S. PATENT DOCUMENTS

| | | | |
|---|---|---|---|
| 4,132,644 A | 1/1979 | Kolberg | 210/85 |
| 4,178,240 A | 12/1979 | Pinkerton | 417/404 |

(List continued on next page.)

FOREIGN PATENT DOCUMENTS

| | | |
|---|---|---|
| EP | 0373455 | 6/1990 |
| FR | 2397197 | 2/1979 |

OTHER PUBLICATIONS

Sartorius Hemoprocessor 40020 Operating Instructions, Sep. 1984, Sartorius GmbH, Gottengen, Germany.*

(List continued on next page.)

Primary Examiner—John Kim
(74) Attorney, Agent, or Firm—Wood, Herron & Evans, L.L.P.

(57) ABSTRACT

A multipurpose hemofiltration system and method are disclosed for the removal of fluid and/or soluble waste from the blood of a patient. The system and method are equally applicable to adult, pediatric and neonatal patients. In one embodiment, the system continuously monitors the weight of infusate in a first reservoir and drained fluid in a second reservoir and compares those weights to corresponding predetermined computed weights. When necessary, the pumping rates of the infusate, drained fluid and blood are adjusted in order to achieve a preselected amount of fluid removal from the patient's blood in a preselected time period. Application of this system and method provide repeatable and highly precise results. Alternatively, predetermined patient parameters can be monitored and the adjustment of pumping rates may be responsive to these monitored parameters. Suitable patient parameters are arterial pressure, central venous pressure, pulmonary arterial pressure, mean arterial pressure, capillary wedge pressure, systemic vascular resistance, cardiac output, mixed venous $O_2$ saturation, arterial $O_2$ saturation, blood pressure, heart rate, patient weight, and hematocrit.

8 Claims, 2 Drawing Sheets

U.S. PATENT DOCUMENTS

| | | | | |
|---|---|---|---|---|
| 4,204,957 A | | 5/1980 | Weickhardt | 210/98 |
| 4,324,663 A | | 4/1982 | Hirel et al. | 210/646 |
| 4,370,983 A | * | 2/1983 | Lichtenstein | 128/630 |
| 4,372,846 A | | 2/1983 | Yamagami et al. | 210/929 |
| 4,582,598 A | | 4/1986 | Bilstad et al. | 210/101 |
| 4,606,826 A | | 8/1986 | Sano et al. | 210/929 |
| 4,684,460 A | | 8/1987 | Issautier | 210/90 |
| 4,710,164 A | * | 12/1987 | Levin et al. | 210/646 |
| 4,728,433 A | | 3/1988 | Buck et al. | 210/646 |
| 4,767,399 A | | 8/1988 | Bollish | 604/5 |
| 4,769,132 A | | 9/1988 | Patono | 210/86 |
| 4,844,810 A | | 7/1989 | Richalley et al. | 210/646 |
| 4,889,635 A | | 12/1989 | Chevallet | 210/646 |
| 4,923,598 A | | 5/1990 | Schäl | 210/87 |
| 4,980,054 A | | 12/1990 | Lavender | 210/90 |
| 5,200,090 A | | 4/1993 | Ford et al. | 210/739 |
| 5,211,849 A | | 5/1993 | Kitaevich et al. | 210/645 |
| 5,247,434 A | * | 9/1993 | Peterson et al. | 210/646 |
| 5,326,476 A | * | 7/1994 | Grogan et al. | 210/646 |
| 5,344,568 A | | 9/1994 | Kitaevich et al. | 210/645 |
| 5,679,245 A | * | 10/1997 | Manica | 210/646 |

OTHER PUBLICATIONS

"Monitrial S. Biofiltration Acetate Free" and "Monitrial SC Biofiltration Acetate Free", Hospal (Jan. 1993).*

"Removal of Fluid From the Patient During Hemodialysis," J.H. Holmes & S. Nakamoto, Dept. of Medicine, U. of Colorado, Mar., 1969.

AK–10 System—Operator's Manual for Hemofiltration—BMM 10–1 & HFM 10–1, ©May 1986, Gambro AB, Lund, Sweden.

Hospal Instruction Manual BSM 22 SC, Rev. A, pp. 29, 30 & 57, Mar. 1990.

COBE Centrysystem™ 3 Dialysis Control Unit Operator's Manual, pp. 1–21, 1–22, 3–29, 5–1, 5–2 & 7–9, Sep. 1988.

Sartorius Hemofilter, date unknown.

Sartorius Membranfilter Hemofilter and Hemoprocessor, A New System for Hemofiltration, date unknown.

"Hemofiltration in Perspective," ©Oct. 1989, Gambro AB, Lund, Sweden.

COBE CentrySystem™3—Precise Ultrafiltration Control, ©1987, COBE Laboratories, Inc., Lakewood, Colorado.

Acute Continuous Renal Replacement Therapy, Emil P. Paganini, M.D. (editor), ©1986, Martinus Nijhoff Publishing, Boston, Massachusetts, pp. 91–111.

Hemofiltration, edited by L.W. Henderson et al., ©1986, Springer–Verlag, New York, pp. 83–89.

International Electrotechnical Commission International Standards for Medical Electrical Equipment, Part 2—Particular requirements for safety of hemodialysis equipment, ©1989, Geneva, Switzerland, pp. 1–57.

Intensivbehandlung, Jahrgang 15, Nov. 3, 1990, p. 110.

Y. Kitaevich et al., "Development of a High–Precision Continuous Extracorporeal Hemodiafiltration System", Biomedical Instrumentation & Technology, Mar./Apr. 1993, pp. 150–156.

M.J. Elliott, "Ultrafiltration and Modified Ultrafiltration in Pediatric Open Heart Operations", Ann Thorac Sur 1993;56:1518–22.

* cited by examiner

HEMOFILTRATION SYSTEM AND METHOD BASED ON MONITORED PATIENT PARAMETERS

RELATED APPLICATION

This application is a continuation, of application Ser. No. 08/478,946, filed Jun. 7, 1995 abandoned, which is a continuation-in-part application of U.S. patent application Ser. No. 08/299,899, filed Sep. 1, 1994, abandonded which is a continuation of patent application Ser. No. 08/062,928, filed May 17, 1993, now U.S. Pat. No. 5,344,568 which issued Sep. 6, 1994, which is a continuation of patent application Ser. No. 07/775,183, filed Oct. 11, 1991, now U.S. Pat. No. 5,211,849 which issued May 18, 1993.

FIELD OF THE INVENTION

The present invention is directed to a system and method of blood filtration, and more particularly a continuous system and method for the regulation of the rate of filtration of fluid and/or soluble waste from the blood of a patient based on one or more monitored patient parameters.

BACKGROUND OF THE INVENTION

For various reasons, including illness, injury or surgery, patients may require replacement or supplementation of their natural renal function in order to remove excess fluid or fluids containing dissolved waste products from their blood. Several procedures known for this purpose are dialysis, hemodialysis, hemofiltration, hemodiafiltration and ultrafiltration; another related procedure is plasmapheresis. The specific procedure employed depends upon the needs of the particular patient. For example, dialysis is used to remove soluble waste and solvent from blood; hemofiltration is used to remove plasma water from blood; hemodiafiltration is used to remove both unwanted solute (soluble waste) and plasma water from blood; ultrafiltration is a species of hemofiltration; and plasmapheresis is used to remove blood plasma by means of a plasmapheresis filter. Because the replacement of renal function may affect nutrition, erythropoiesis, calcium-phosphorus balance and solvent and solute clearance from the patient, it is imperative that there be accurate control of the procedure utilized. The accurate control of the rate of removal of intravascular fluid volume is also important to maintain proper fluid balance in the patient and prevent hypotension.

Various systems have been proposed to monitor and control renal replacement procedures. For example, U.S. Pat. No. 4,132,644 discloses a dialysis system in which the weight of dialyzing liquid in a closed liquid container is indicated by a scale. After the dialyzing liquid flows through the dialyzer, the spent liquid is returned to the same container and the weight is again indicated. Since the container receives the original dialyzing liquid plus ultrafiltrate, the amount of ultrafiltrate removed from the patient is equal to the increase in total weight in the container. This system is not driven by a weight measuring device and does not offer precise control of the amount of liquids used in the procedure.

U.S. Pat. No. 4,204,957 discloses an artificial kidney system which utilizes weight measurement to control the supply of substitute fluid to a patient. In this system, the patient's blood is pumped through a filter and the filtrate from the blood is discharged to a measuring vessel associated with a weighing device. A second measuring vessel containing substitute fluid is associated with a second weighing device and is connected to the purified blood line. By means of a pump, the substitute fluid and the purified blood are pumped back to the patient. The first and second weighing devices are coupled to one another by a measuring system in such a way that a fixed proportion of substitute is supplied to the purified blood stream from the second measuring vessel depending an the weight of the filtrate received in the first measuring vessel. This system does not utilize circulating dialysate fluid in the blood filtration.

U.S. Pat. No. 4,767,399 discloses a system for performing continuous arteriovenous hemofiltration (CAVH). The disclosed system relies upon utilizing a volumetric pump to withdraw a desired amount of fluid from the patient's blood and return a selected amount of fluid volume to the patient.

U.S. Pat. No. 4,923,598 discloses an apparatus for hemodialysis and hemofiltration which comprises an extracorporeal blood circuit including a dialyzer and/or filter arrangement. The system determines fluid withdrawal per unit time and total amount of fluid withdrawn by utilizing flow sensors in conjunction with an evaluating unit located upstream and downstream of the dialyzer or filter arrangement in the blood circuit.

U.S. Pat. No. 4,728,433 discloses a system for regulating ultrafiltration by differential weighing. The system includes a differential weighing receptacle having an inlet chamber and an outlet chamber which allows a fixed amount of fresh dialysate, by weight, to flow through the hemodialyzer. This system operates in a sequence of weighing cycles during which the amount of ultrafiltrate removed from the blood may be calculated. Additionally, the ultrafiltration rate for each weighing cycle may be calculated. This system provides a mechanism for determining and regulating the amount of ultrafiltrate removed from the blood while delivering dialysate to the patient in alternating fill and drain cycles of the inlet and outlet chambers of the differential weighing receptacle.

The need exists for a multipurpose renal function replacement/supplementation system which is accurate, reliable, capable of continuous, long-term operation, and which can be used effectively on adult, pediatric and neonatal patients.

SUMMARY OF THE INVENTION

The present invention is directed to a multipurpose system and method for removal of fluid and/or soluble waste from the blood of a patient: ultrafiltration only, hemodiafiltration, hemodiafiltration and ultrafiltration, and plasmapheresis with or without fluid replacement. The system and method of the present invention can provide reliable, long term operation (5–10 days) with a great degree of accuracy (on the order of +−2 grams regardless of the total volume of fluid passing through the system). The system and method of the invention are advantageous because of the multipurpose nature thereof, the repeatability and accuracy of the processes, and the simultaneous, continuous flow of fluids in an extracorporeal blood circuit, while being equally applicable to adult, pediatric and neonatal patients.

As used herein the term "hemofiltration" is to be broadly construed to include hemodialysis, hemofiltration, hemodiafiltration, ultrafiltration and plasmapheresis processes. As used herein, the term "infusate" is defined to include dialysate fluid or any other replacement fluids which may be supplied to the patient as a part of the hemofiltration procedures.

In a preferred embodiment, the system of the present invention includes a hemofilter, a blood pump for pumping blood from a patient through the hemofilter and back to the patient, and suitable tubing for carrying the pumped blood to and from the patent. The system further includes a first reservoir for maintaining a supply of infusate, a first weighing means for continuously monitoring the weight of the infusate and generating weight data signals correlated to the monitored weight, and a first pump for pumping the infusate from the first reservoir to the hemofilter or appropriate blood tubing access port. A second reservoir receives drained fluid (e.g., spent infusate or ultrafiltrate, including the fluids and solutes removed from the blood) from the hemofilter, and a second weighing means monitors the weight of the drained fluid and generates weight data signals correlated to the monitored weight. A second pump pumps the drained fluid from the hemofilter to the second reservoir. The system also includes a computerized controller operably connected to the blood pump, the infusate pump, the drain pump and the first and second weighing means.

The controller periodically, but on an ongoing basis during the treatment, interrogates at predetermined intervals the weight data signals that are continuously generated by the first and second weighing means and is designed to determine therefrom the weight of infusate and drained fluid in the first and second reservoirs at the predetermined intervals. The rate of fluid withdrawal from the blood is also determined. The controller compares the infusate and drained fluid weights to corresponding predetermined computed weights in the memory of the controller, and, when necessary, the controller generates control signals which automatically adjust the pumping rates of the infusate and drained fluid pumps in order to achieve a preselected amount of fluid removal from the patient's blood. Additionally, the controller is programmed to operate the infusate and drained fluid pumps only when the blood pump is operating. Furthermore, the blood pump is operably connected to and is responsive to control signals generated by the controller in response to or independent of the weight data signals to vary the flow rate of the blood through the hemofilter as required to achieve the desired level of fluid removal from the blood.

In an alternative embodiment, the computer controller is, by initial selection of the operator, interfaced with one or more of the various monitoring systems that are operably connected to the patient. These monitoring systems, which are well known in the art, generate and output data signals corresponding to the monitored patient parameters, and the computer controller receives such data signals. During the hemofiltration operation, the interfaced parameters are constantly monitored; however, the controller only responds to specific parameter data that corresponds to the patient parameters selected by the operator. The patient parameters which may be monitored and interfaced with the computer controller include the following: arterial pressure, central venous pressure, pulmonary arterial pressure, mean arterial pressure, capillary wedge pressure, systemic vascular resistance, cardiac output, $O_2$ saturation (mixed venous or arterial), blood pressure, heart rate, patient weight, external infusion rates, and hematocrit. Numerous of these parameters may be monitored and corresponding output data signals generated in known manner utilizing an indwelling intravenous or intra-arterial catheter. The remaining parameters are monitored and data signals are generated by means well known in the art. The operator will select one or more of the above parameters to interface with the controller which will then periodically, but on an ongoing basis during treatment, interrogate at predetermined intervals the parameter data signals that are continuously generated by the interfaced monitoring system(s). The controller then evaluates the parameter data and in response thereto, when necessary, the controller generates control signals which automatically adjust the pumping rates of the infusate, drained fluid and blood pumps so as to achieve a preselected amount of fluid removal from the patient's blood.

It will be appreciated that the system of the present invention may utilize a combination of monitoring and responding to the infusate and drained fluid weight data signals, as described in connection with the first embodiment hereinabove, along with one or more of the other patient parameters interfaced to the controller.

By way of specific examples, in connection with monitoring the patient's weight, the computer controller may be interfaced with a bed scale which provides continuous values for the patient's weight. In response to the overall patient weight data signals, the computer controller may control the infusate and/or drained fluid pumps to achieve a predesigned protocol for decreasing or increasing the patient's weight over time. The change in patient's weight (by increase or decrease) can be accomplished in either a linear or non-linear (such as curvilinear) manner with respect to time by appropriate pump control. Similarly, the computer may be interfaced with a continuous read-out device of the patient's $O_2$ saturation and the controller will receive, evaluate and respond to the $O_2$ saturation data by controlling the infusate, drained fluid and blood pumping rates accordingly.

In connection with all of the above-described monitored parameters, the computer controller will receive data signals corresponding and relating to each particular selected parameter from an appropriate signal generating device or source operably connected to the patient. The controller will then, after periodic interrogation, compare the interrogated values with predetermined desired values and will automatically make the appropriate, predetermined changes in the infusate, drained fluid and blood pumping rates in response to the monitored signals. Furthermore, more than one of the above-referenced parameters can be continuously monitored simultaneously and the computer may be programmed with a hierarchy to consider one or more specific parameters rather than others and will respond with the appropriate and desired adjustments in infusate, drained fluid and blood pumping rates based on those selected parameters.

The computer controller is designed and programmed to adjust the pumping rates (pump speed) of the infusate, drained fluid and blood pumps so as to provide a linear response or a non-linear (curvilinear) response to the observed changes in the selected monitored parameters. In this regard, "linear" is defined to mean a fixed, non-exponential change, and "non-linear" or "curvilinear" means anything other than linear. The selection of linear versus non-linear response profile is made by the operator of the system depending on the needs of the patient. For example, in certain situations it may be desirable to have an initially fast fluid removal rate that decreases over time. In that case a curvilinear or exponential response would be utilized. In other circumstances, consistent or constant fluid removal over time is desired, and so a linear response profile is selected. It is further contemplated that at the election of the operator the computer controller may combine linear and curvilinear response signals so as to tailor the pump rates to achieve a desired response profile. For example, a non-linear initial response period for fast initial fluid removal, followed by a linear response period for ongoing fluid removal at a consistent rate.

In yet another alternative embodiment, the computer controller receives data signals from one or more patient infusion pumps that are otherwise independent of the hemofiltration system. These infusion pumps are used for infusion to the patient of intravenous fluids, medications, parenteral nutrition and/or blood products. By monitoring the data output from the independent infusion pumps, the extraneous total fluid volume per unit time may be ascertained. The controller will then, as required, change the pumping rates of the system infusate, drained fluid and blood pumps, as necessary, so as to alter the ultrafiltration rate and/or infusate fluid rate automatically in response to changes in intravenous fluid therapy. This facilitates independent patient management while hemofiltration is being performed. Proper coordination of the controller with the independent infusion pumps allows the desired or targeted fluid removal goals by hemofiltration to be achieved automatically in concordance with ongoing intravenous fluid therapy.

In a preferred embodiment of the method of the present invention, blood from a patient is pumped through a hemofilter and a supply of infusate, which is maintained in a first reservoir, is pumped from the first reservoir through the hemofilter, countercurrent to the blood. The weight of infusate in the first reservoir is continuously monitored and data signals correlated to that weight are generated. Drained fluid (e.g., spent infusate) is pumped from the hemofilter and is received in a second reservoir. The weight of the drained fluid in the second reservoir is continuously monitored and weight data signals correlated thereto are generated. The signals correlated to the weight of infusate and drained fluid are interrogated at regular intervals (for example every minute) by a system controller and are compared to corresponding predetermined computed weights in the memory of the controller. The controller determines the amount and rate of fluid withdrawal from the patient's blood. If those values differ from preselected, preprogrammed desired values, the controller generates control signals which independently adjust the pumping rates of the infusate and drained fluid pumps so as to achieve the desired amount of fluid removal. The control signals may also control the blood pumping rate.

In an alternative embodiment of the method of the present invention, independent of or in addition to the infusate and drained fluid weight monitoring and pump control, the computer controller may be interfaced with one or more of the previously discussed monitoring systems. In this embodiment, the controller will receive, evaluate and respond to the selected patient parameter data by generating appropriate, responsive control signals by which the infusate, drained fluid and blood pumping rates are controlled to achieve the desired amount of fluid removal. This may be accomplished in combination with or independent of the infusate and drained fluid weight monitoring.

The advantages of the system and method of the present invention are achieved at least in part due to the continuous monitoring and periodic interrogation of the fluid weights, and other selected patient parameters, and the adjustment of fluid pumping rates in response thereto, including the blood pumping rate, so as to achieve ideal or nearly ideal fluid removal and replacement if necessary from a patient's blood. Further features and advantages of the system and apparatus of the present invention will become apparent with reference to the Figure and the detailed description which follows.

DESCRIPTION OF THE INVENTION

Figure 1:
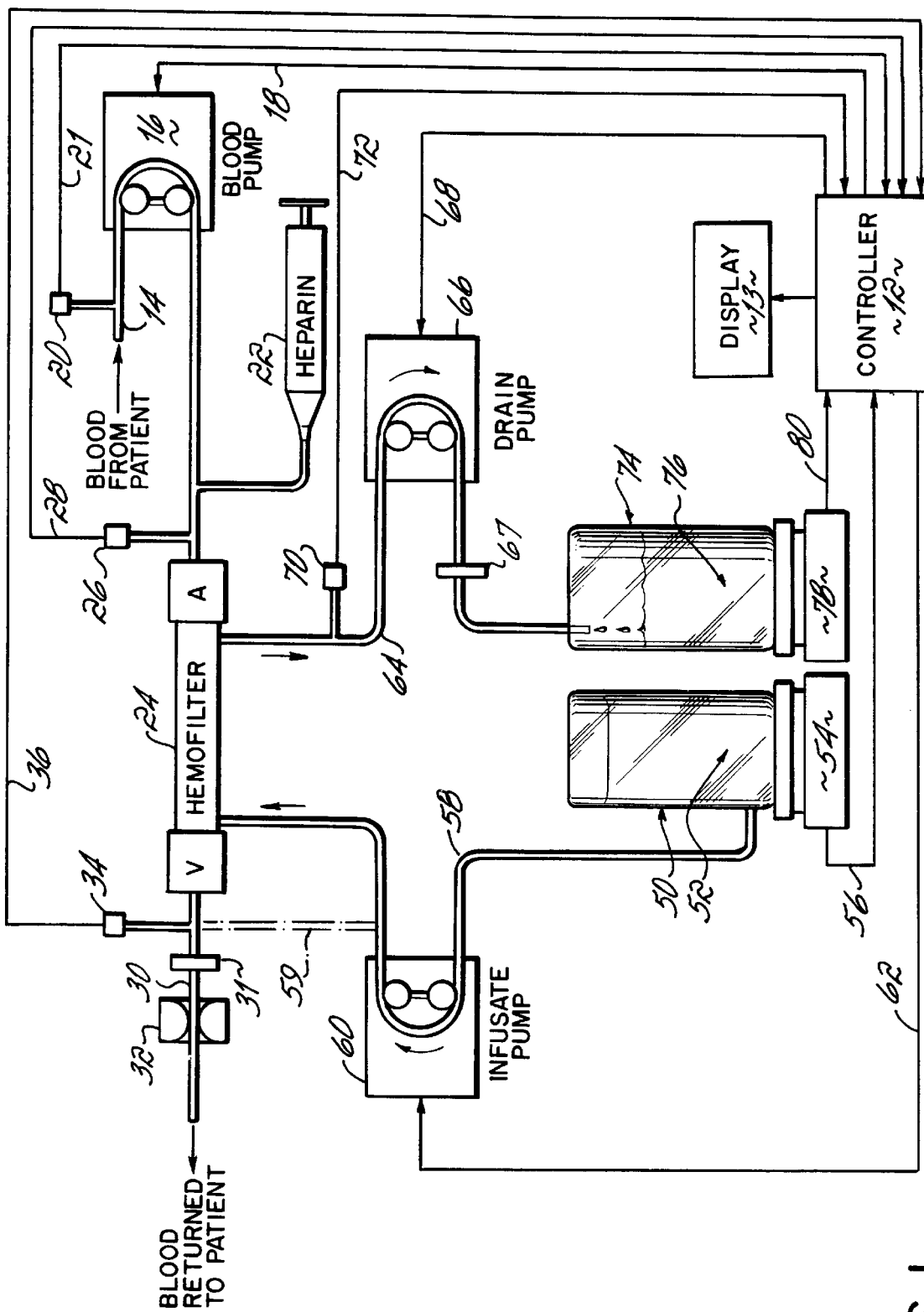
FIG. 1 is a diagrammatic representation of one embodiment of the system of the present invention; a variation is shown in phantom.

FIG. 1 shows a diagrammatic representation of a preferred embodiment of the system of the present invention. The portion of FIG. 1 shown in phantom represents an alternative embodiment of the present invention which will be described hereinbelow. Hemofiltration system 10 is operated and controlled by a suitable controller designated generally as 12. Controller 12 may be a programmable computer such as a COMPAQ 386/S having a display 13 and is operably connected to various components of hemofiltration system 10, as will be described in greater detail hereinafter.

In operation, blood is pumped from a patient (not shown), which may be an adult, pediatric or neonatal patient, through a suitable catheter (not shown) and input tubing 14 by means of a blood pump 16. Blood pump 16, which is preferably of the roller type, is operably connected to controller 12 by line 18. One suitable blood pump is the RS-7800 Minipump manufactured by Renal Systems, Minneapolis, Minn. Input tubing 14 through which the patient's blood is pumped preferably includes a pressure transducer 20 upstream of pump 16. Pressure transducer 20 is operably connected to controller 12 via line 21. Means are included downstream of blood pump 16 for accessing input tubing 14 to enable the injection or infusion of desired fluids, including medications and anticlotting compounds such as heparin, into the patient's blood. The injection or infusion of such fluids to the blood may be accomplished in any suitable manner; FIG. 1 shows diagrammatically a syringe and tube arrangement 22, but it will be appreciated that other means could be employed for the same purpose.

The patient's blood is pumped through hemofilter 24 by blood pump 16. Filters of the type suitable for use in the system of the present invention are readily available; one example of a suitable hemofilter is the Diafilter manufactured by AMICON, Denvers, Mass. Where the present system is used to perform plasmapheresis, a suitable plasmapheresis filter such as the Plasmaflo manufactured by Parker Hannifin, Irvine, Calif. can be employed.

Input tubing 14 includes a second pressure transducer 26 slightly upstream of hemofilter 24. Pressure transducer 26 is operably connected to controller 12 via line 28. The patient's blood exits hemofilter 24, passes through output tubing 30 and is returned to the patient via any suitable means such as a venous catheter arrangement (not shown). Output tubing 30 preferably includes a suitable blood flow detector 31 which verifies that there is blood flow in the system and an air bubble/foam control device such as air bubble clamp 32 to prevent the passage of air bubbles to the patient. Blood flow detector 31 and air bubble clamp 32 may be operably connected (not shown) to controller 12 or directly to the pumps to interlock all pumps upon detection of any air bubbles in the blood or upon the cessation of blood flow. A suitable foam-bubble detector is the RS-3220A manufactured by Renal Systems. Output tubing 30 also preferably includes a pressure transducer 34 immediately downstream of hemofilter 24. Pressure transducer 34 is operably connected to controller 12 via line 36.

A first reservoir 50 maintains a supply of suitable dialysate or other fluid, referred to herein generally as infusate 52. The infusate-containing reservoir 50 is supported by a weighing device such as electronic scale 54 which is operably connected to controller 12 via line 56. Infusate 52 is pumped from reservoir 50 via tubing 58 by means of infusate pump 60, which is preferably of the roller variety. A suitable pump for this purpose is a 3½ Roller Pump manufactured by PEMCO, Cleveland, Ohio. Infusate pump 60 is operably connected to controller 12 via line 62 and pumps infusate 52 through hemofilter 24 countercurrent to the blood pumped therethrough. In accordance with known principles, infusate 52 may extract certain components (fluids and/or soluble waste) from the blood passing through hemofilter 24. The fluid drained from hemofilter 24 includes spent infusate and the components removed from the blood, which are referred to herein as drained fluid 76. In an alternative embodiment wherein system 10 is used as a fluid or plasma replacement system, e.g., to perform plasmapheresis, the infusate (which may be blood plasma) from reservoir 50 is pumped via tubing 59 (shown in phantom) to blood output tubing 30, thereby replacing the fluid volume removed from the blood. In this embodiment, the drained fluid 76 from hemofilter or plasmapheresis filter 24 does not include any spent infusate since the infusate is pumped directly to blood output tubing 30 and supplied to the patient.

The drained fluid 76 is pumped from hemofilter 24 through outlet tubing 64 by means of drain pump 66, which is preferably a roller-type pump, and may be the same as infusate pump 60. Drain pump 66 is operably connected to controller 12 via line 68. Output tubing 64 preferably includes a pressure transducer 70 downstream of hemofilter 24, but upstream of drain pump 66. Pressure transducer 70 is operably connected to controller 12 via line 72. Output tubing 64 also preferably includes a blood leak detector 67 which detects the presence of blood in the drained fluid 76, as may occur if hemofilter 24 ruptures. A suitable blood leak detector is sold by COBE, Lakewood, Colo. as model 500247000. Blood leak detector 67 may be operably connected (not shown) to controller 12 or directly to the pumps to interlock all pumps upon the detection of blood in the drained fluid. Drained fluid 76 pumped from hemofilter 24 is pumped into a second reservoir 74 which collects the drained fluid. Second reservoir 74 is supported by a weighing device such as electronic scale 78, which is operably connected to controller 12 via line 80.

Scales 54 and 78, which may be model 140 CP sold by SETRA of Acton, Mass. continuously generate weight data signals correlated to the weight of infusate and drained fluid contained in reservoirs 50 and 74, respectively. Those weight data signals are continuously fed to controller 12, to which the scales are linked through an RS-232 interface. It will be appreciated that a single scale could be utilized in place of the two scales whereby the weight differential between reservoir 50 and 74 is monitored and a corresponding data signal is generated. Pressure transducers 20, 26, 34 and 70 all continuously measure the pressure at their respective locations in hemofiltration system 10 and generate pressure data signals correlated thereto which are fed to controller 12. A suitable type of pressure transducer is model number 042-904-10 sold by COBE of Lakewood, Colo. When certain predetermined alarm or danger conditions exist in the system 10, as represented by the pressure data signals, the controller will either adjust the infusate, drained fluid, or blood pumping rate, or a combination thereof, or will shut the system down entirely.

Controller 12 is preferably a programmable computer that is capable of sending and receiving signals from auxiliary equipment including pressure transducers 20, 26, 34 and 70, first and second scales 54 and 78, respectively, and blood pump 16, infusate pump 60, and drain pump 66. In operation, controller 12 interrogates, at regular intervals, the weight data signals generated by first and second scales 54 and 78. From these signals, controller 12 determines the weight of infusate and drained fluid in the first and second reservoirs 50 and 74 at that point in time, and compares those weights to corresponding predetermined computed weights which have been programmed into and are stored by controller 12. By monitoring the weight of infusate in reservoir 50 and the weight of drained fluid in reservoir 74 at regular intervals, the rate of change of those weights and the rate of hemofiltration can be calculated by the computer portion of controller 12. When the weights deviate from the predetermined computed weights and/or the rate of hemofiltration deviates from a preselected, preprogrammed desired rate, controller 12 generates control signals which control or adjust the rates at which blood pump 16, infusate pump 60 and drain pump 66 are operated, as necessary, to adjust the hemofiltration rate to the desired rate, or to stop the pumps when preselected limits have been reached. This is accomplished in a continuous manner; i.e., continuous weight data signal generation, periodic interrogation of those weight data signals and computation of the required weight and/or rate information, comparison to predetermined computed values and automatic adjustment of the pumping rates of the pumps, as necessary, to achieve the desired amount and/or rate of hemofiltration.

Controller 12 is programmed so that infusate pump 60 and drain pump 66 are operated only when blood pump 16 is being operated. In the case when ultrafiltration is being performed, the pumping rate of drain pump 66 must equal the pumping rate of infusate pump 60 plus the desired ultrafiltration rate.

Controller 12 continuously receives pressure data signals from pressure transducers 20, 26, 34 and 70 and is programmed to generate alarm signals when high and low pressure limits are exceeded at any of the monitored locations. Furthermore, an alarm signal is generated when the pressure differential across hemofilter 24 exceeds a predetermined upper limit, as monitored specifically by pressure transducers 26, 34 and 70. Additionally, controller 12 may stop the pumps when preselected pressure limits (high or low) are exceeded, as for example may occur if the system tubing becomes occluded or ruptures or if pump occlusion occurs. Finally, controller 12 may signal when the infusate level in reservoir 50 reaches a predetermined lower limit and when the drained fluid level in reservoir 76 reaches a predetermined upper limit. Hemofiltration system 10 may also include suitable blood warmer and infusate warmer devices (not shown) to adjust and/or maintain the blood and infusate temperatures at desired levels. Such devices may also generate alarm signals when the fluid temperatures are outside of preselected limits.

Display 13 offers updated display of measured and computed parameters such as pressures, pressure differentials, temperatures, flow rates and amounts of infusate, drain and ultrafiltration, and alarm conditions. Controller 12 generates both visual and audible alarms and all the pumps are interlocked to prevent operation thereof under alarm conditions. Users have the option of disabling or unabling the alarms (the audible part of the alarm and its interlock with the pumps) to perform a procedure under close supervision. A printer (not shown) is operably connected (not shown) to controller 12 to generate a hard copy of procedural data currently displayed or stored at regular intervals, at the completion of a procedure or at any desired time.

Hemofiltration system 10 can be operated in one of two modes: 1) a manual mode wherein the pumping rates of blood pump 16, infusate pump 60 and drain pump 66 are provided by controller 12 when fixed voltages are applied; and 2) an automatic mode wherein the pumps are controlled by controller 12 when the desired hemofiltration amount or rate has been programmed into the controller. The automatic mode allows the system to be paused and later continued without losing previously measured and computed data.

Figure 2:
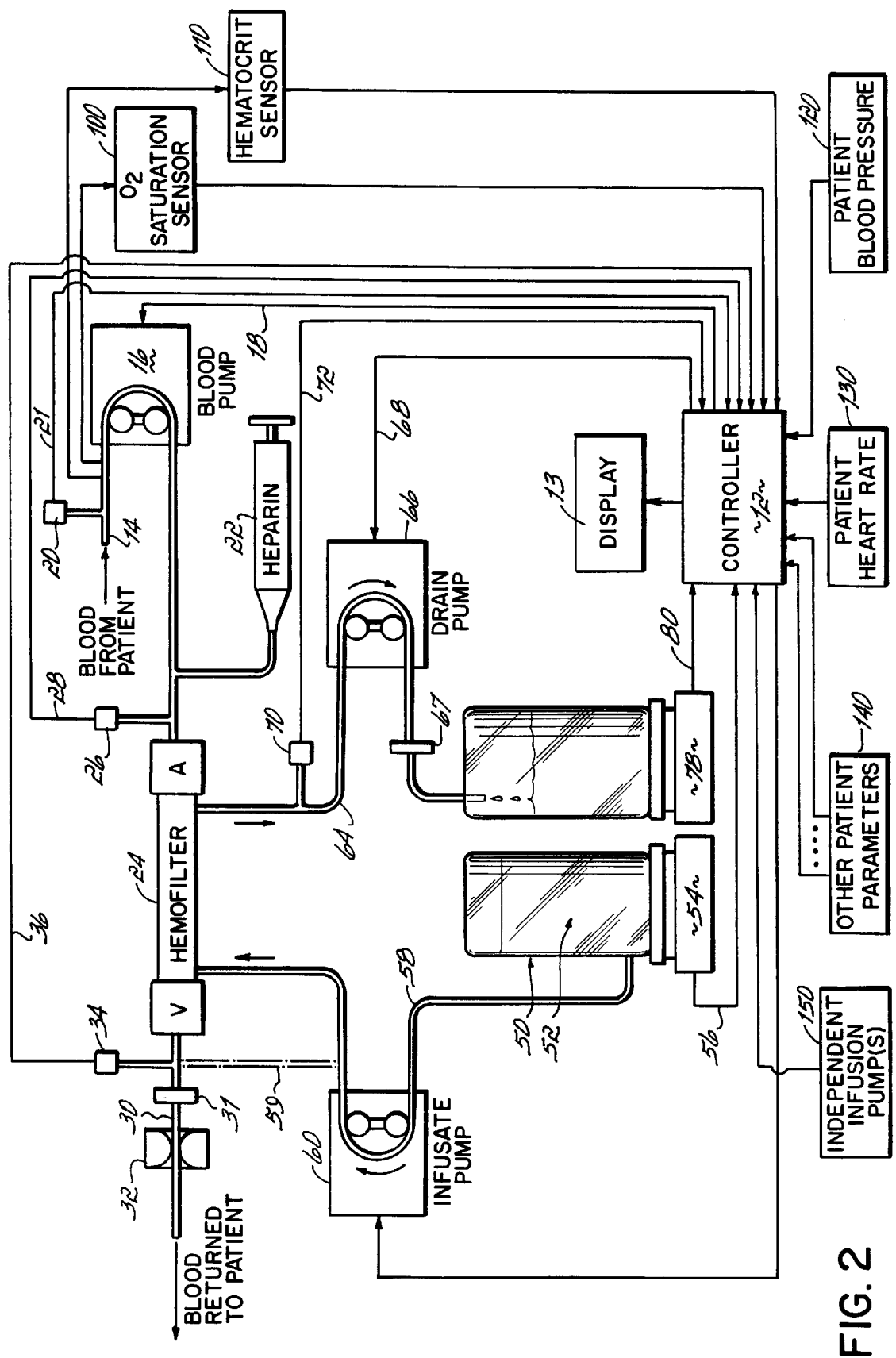
FIG. 2 is a diagrammatic representation of an alternative embodiment of the system of the present invention.

FIG. 2 shows a diagrammatic representation of several alternative embodiments of the system 10 of the present invention. Because of the commonality of many of the system components in FIG. 2 vis-a-vis the system depicted in FIG. 1, like reference numerals are intended to indicate like components. Furthermore, the system components in FIGS. 2 operate in the same manner as the corresponding system components shown in FIG. 1 and described hereinabove.

The system of FIG. 2 further includes interfaces between controller 12 and monitoring systems which generate parameter data signals corresponding to selected patient parameters such as $O_2$ saturation 100, hematocrit 110, patient blood pressure 120, patient heart rate 130 and numerous other patient parameters (designated generally as 140), which other parameters may be one or more of the following: arterial pressure, central venous pressure, pulmonary arterial pressure, mean arterial pressure, capillary wedge pressure, systemic vascular resistance, cardiac output, and patient weight. While the $O_2$ saturation sensor 100 and hematocrit sensor 110 are shown as being connected to the patient blood line 14, these parameters can also be monitored by means associated directly with the patient rather than via blood tubing 14. In fact, whereas venous $O_2$ saturation could be measured as indicated, arterial $O_2$ saturation would require the monitor to be located elsewhere. The overall patient weight parameter can be monitored utilizing a standard patient bed scale (not shown) as is well known in the art.

During the hemofiltration operation, one or more of the various patient parameters will be monitored continuously and the controller will, at the selection of the operator, be responsive to selected parameter data supplied to the controller. The parameter data may be evaluated and responded to by the controller independent of the infusate and drained fluid weight data signals; i.e., the system may operate and respond based on one or more of the selected parameters and not the weight data signals; or the system may respond to a combination of the weight data signals and one or more selected specific parameters.

One or more independent patient infusion pumps 150 may be interfaced with computer controller 12 to supply data signals correlated to the infusion to the patient of intravenous fluids, medications, parenteral nutrition and/or blood products. The controller 12 may evaluate this data and make modifications to the infusate, drained fluid and blood pumping rates so as to compensate for the extraneous fluid being delivered to the patient by means of the infusion pumps. In this regard, the overall fluid balance in the patient can be managed concurrent with a hemofiltration operation.

It will be appreciated by persons skilled in the art that various modifications can be made to the systems and methods of the present invention without departing from the scope thereof which is defined by the appended claims.

What is claimed is:

1. Continuous hemofiltration system for removal of fluid from the blood of a patient, comprising:
    a hemofilter;
    a first pump for pumping blood from a patient through said hemofilter and back to the patient;
    a first reservoir for maintaining a supply of infusate;
    a first scale for monitoring the weight of the infusate and generating weight data signals correlated thereto;
    a second pump for pumping the infusate from said first reservoir to said hemofilter;
    a second reservoir for receiving drained fluid from said hemofilter;
    a second scale for monitoring the weight of the drained fluid and generating weight data signals correlated thereto;
    a third pump for pumping the drained fluid from said hemofilter to said second reservoir;
    at least one monitor for monitoring a predetermined patient parameter selected from the group consisting of arterial pressure, central venous pressure, pulmonary arterial pressure, mean arterial pressure, capillary wedge pressure, systemic vascular resistance, cardiac output, mixed venous $O_2$ saturation, arterial $O_2$ saturation, blood pressure, heart rate, patient weight, and hematocrit, and generating parameter data signals correlated thereto; and
    a computer controller operably connected to said first pump and to each of said second and third pumps, said first and second scales and said at least one patient parameter monitor;
    said controller
        receiving said weight data signals generated by said first and second scales and said parameter data signals generated by said at least one parameter monitor,
        determining from said weight data signals the weight of infusate and drained fluid in said first and second reservoirs, respectively, at regular intervals,
        comparing those weights to corresponding predetermined computed weights,
        determining from said parameter data signals the corresponding patient parameter data,
        comparing the parameter data to corresponding predetermined data, and
        generating control signals in response to said weight data and parameter data signals, whereby said control signals adjust continuously and automatically as necessary on an ongoing basis during hemofiltration the rates of pumping one or more of the infusate, drained fluid and blood while the pumps are pumping during hemofiltration so as to remove a preselected amount of fluid from the blood over a preselected time period.

2. A hemofiltration system according to claim 1 further comprising:
    an interface with one or more infusion pumps supplying fluid to the patient, said controller receiving infusion data signals from the one or more infusion pumps.

3. Continuous hemofiltration system for removal of fluid from the blood of a patient, comprising:
    a hemofilter;
    a first pump for pumping blood through said hemofilter and back to the patient;
    a supply of infusate;
    a second pump for pumping the infusate to said hemofilter;
    a receptacle for receiving drained fluid from said hemofilter;
    a third pump for pumping the drained fluid from said hemofilter to said receptacle;

at least one monitor for monitoring a predetermined patient parameter selected from the group consisting of arterial pressure, central venous pressure, pulmonary arterial pressure, mean arterial pressure, capillary wedge pressure, systemic vascular resistance, cardiac output, mixed venous $O_2$ saturation, arterial $O_2$ saturation, blood pressure, heart rate, patient weight, and hematocrit, and generating parameter data signals correlated thereto; and a computer controller operably connected to said first pump, said second and third pumps, and said at least one patient parameter monitor;

said controller
  receiving said parameter data signals generated by said at least one parameter monitor,
  determining from said parameter data signals the corresponding patient parameter data,
  comparing the parameter data to corresponding predetermined data, and
  generating control signals in response to said parameter data signals, whereby said control signals adjust continuously and automatically as necessary on an ongoing basis during hemofiltration the rates of pumping one or more of the infusate, drained fluid and blood while the respective pumps are pumping during hemofiltration so as to remove a preselected amount of fluid from the blood over a preselected time period.

4. Hemofiltration method for removal of fluid from the blood of a patient, comprising:

pumping blood from a patient through a hemofilter and back to the patient;

maintaining a supply of infusate in a first reservoir;

pumping the infusate to the hemofilter;

monitoring the weight of the infusate and generating weight data signals correlated thereto;

pumping drained fluid from the hemofilter into a second reservoir;

monitoring the weight of the drained fluid and generating weight data signals correlated thereto;

monitoring at least one predetermined patient parameter selected from the group consisting of arterial pressure, central venous pressure, pulmonary arterial pressure, mean arterial pressure, capillary wedge pressure, systemic vascular resistance, cardiac output, mixed venous $O_2$ saturation, arterial $O_2$ saturation, blood pressure, heart rate, patient weight, and hematocrit, and generating parameter data signals correlated thereto; and controlling the pumping rates of the blood, infusate and drained fluid by means of a programmed computer, said computer being responsive to the infusate and drained fluid weight data signals and to said parameter data signals, said computer
  receiving said weight data signals and said parameter data signals,
  determining from said weight data signals, at regular intervals, the weight of infusate in the first reservoir and the weight of drained fluid in the second reservoir,
  comparing those weights to corresponding predetermined computer weights,
  determining from said parameter data signals the corresponding patient parameter data,
  comparing the parameter data to corresponding predetermined data, and
  generating control signals in response to said weight data and parameter data signals, whereby said control signals adjust continuously and automatically as necessary on an ongoing basis during hemofiltration the rates of pumping one or more of the infusate, drained fluid and blood while the respective pumps are pumping during hemofiltration so as to remove a preselected amount of fluid from the blood.

5. A hemofiltration method according to claim 4 further comprising:
  interfacing said computer with one or more infusion pumps supplying fluid to the patient, said computer receiving infusion data signals from the one or more infusion pumps.

6. The hemofiltration method of claim 4 wherein said control signals adjust the pumping rates of one or more of the infusate, drained fluid and blood pumps such that the fluid removed from the patient's blood is removed in a linear profile over time.

7. The hemofiltration method of claim 4 wherein said control signals adjust the pumping rates of one or more of the infusate, drained fluid and blood pumps such that the fluid removed from the patient's blood is removed in a non-linear profile over time.

8. Hemofiltration method for removal of fluid from the blood of a patient, comprising:

pumping blood from a patient through a hemofilter and back to the patient;

maintaining a supply of infusate;

pumping the infusate to the hemofilter;

pumping drained fluid from the hemofilter into a reservoir;

monitoring at least one predetermined patient parameter selected from the group consisting of arterial pressure, central venous pressure, pulmonary arterial pressure, mean arterial pressure, capillary wedge pressure, systemic vascular resistance, cardiac output, mixed venous $O_2$ saturation, arterial $O_2$ saturation, blood pressure, heart rate, patient weight, and hematocrit, and generating parameter data signals correlated thereto; and controlling the pumping rates of the blood, infusate and drained fluid by means of a programmed computer, said computer being responsive to said parameter data signals, said computer
  receiving said parameter data signals,
  determining from said parameter data signals the corresponding patient parameter data,
  comparing the parameter data to corresponding predetermined data, and
  generating control signals in response to said parameter data signals, whereby said control signals adjust continuously and automatically as necessary on an ongoing basis during hemofiltration the rates of pumping one or more of the infusate, drained fluid and blood while the respective pumps are pumping during hemofiltration so as to remove a preselected amount of fluid from the blood.

\* \* \* \* \*